United States Patent
Tajima et al.

(10) Patent No.: US 12,269,955 B2
(45) Date of Patent: Apr. 8, 2025

(54) PARTICULATE COMPOSITION, LIQUID COMPOSITION, METHOD FOR PRODUCING PARTICULATE COMPOSITION, SURFACE MODIFYING AGENT, AND METHOD FOR IMPROVING WATER DISPERSIBILITY

(71) Applicant: KANAGAWA UNIVERSITY, Kanagawa (JP)

(72) Inventors: Kazuo Tajima, Kanagawa (JP); Yoko Imai, Kanagawa (JP); Kana Miyasaka, Kanagawa (JP)

(73) Assignee: KANAGAWA UNIVERSITY, Kanagawa (JP)

( * ) Notice: Subject to any disclaimer, the term of this patent is extended or adjusted under 35 U.S.C. 154(b) by 221 days.

(21) Appl. No.: 16/478,035

(22) PCT Filed: Nov. 10, 2017

(86) PCT No.: PCT/JP2017/040635
§ 371 (c)(1),
(2) Date: Jul. 15, 2019

(87) PCT Pub. No.: WO2018/135108
PCT Pub. Date: Jul. 26, 2018

(65) Prior Publication Data
US 2019/0367739 A1    Dec. 5, 2019

(30) Foreign Application Priority Data
Jan. 17, 2017 (JP) ................. 2017-006136

(51) Int. Cl.
| | | |
|---|---|---|
| *C09C 3/08* | (2006.01) |
| *A61K 8/02* | (2006.01) |
| *A61K 8/14* | (2006.01) |
| *A61K 8/19* | (2006.01) |
| *A61K 8/29* | (2006.01) |
| *A61K 8/36* | (2006.01) |
| *A61K 8/37* | (2006.01) |
| *A61K 8/58* | (2006.01) |
| *A61K 8/86* | (2006.01) |
| *A61Q 1/00* | (2006.01) |
| *A61Q 1/02* | (2006.01) |
| *A61Q 17/04* | (2006.01) |
| *B01J 13/00* | (2006.01) |
| *C09C 1/00* | (2006.01) |

(Continued)

(52) U.S. Cl.
CPC .............. *C09C 3/08* (2013.01); *A61K 8/14* (2013.01); *A61K 8/19* (2013.01); *A61K 8/37* (2013.01); *A61Q 1/02* (2013.01); *C09C 1/00* (2013.01); *C09C 3/063* (2013.01); *C09D 5/02* (2013.01); *C09D 7/62* (2018.01); *C09D 7/63* (2018.01); *C09D 7/66* (2018.01); *C09D 17/00* (2013.01); *C09K 23/00* (2022.01); *C09K 23/002* (2022.01); *A61K 2800/622* (2013.01); *C01P 2002/84* (2013.01); *C01P 2004/04* (2013.01)

(58) Field of Classification Search
CPC ...... A61K 8/14; A61K 8/19; A61K 2800/412; A61K 2800/612; A61K 2800/622; A61K 8/0241; A61K 8/29; A61K 8/361; A61K 8/37; A61K 8/585; A61K 8/86; B01J 13/00; C09C 1/24; C09C 3/063; A61Q 1/02; A61Q 17/04; A61Q 1/00; B01F 17/0007; B01F 17/0021; B01F 17/0042
See application file for complete search history.

(56) References Cited

U.S. PATENT DOCUMENTS

| | | |
|---|---|---|
| 4,622,074 A | 11/1986 | Miyoshi et al. |
| 6,482,441 B1 | 11/2002 | Hasegawa et al. |

(Continued)

FOREIGN PATENT DOCUMENTS

| | | |
|---|---|---|
| JP | S60190705 A | 9/1985 |
| JP | 2001072527 A | 3/2001 |

(Continued)

OTHER PUBLICATIONS

Hisatsugu et al.; "Dissolution of Human Gallstone"; Journal of Japanese Surgery; vol. 2, No. 2, pp. 62-72; published 1972.*

(Continued)

*Primary Examiner* — Jeffrey T. Palenik
(74) *Attorney, Agent, or Firm* — CANTOR COLBURN LLP (57) ABSTRACT

Provided are: a particulate composition which exhibits high water dispersibility regardless of the kind of solid particles; and a method for producing this particulate composition. Also provided are: a liquid composition; a surface modifying agent; and a method for improving water dispersibility. The present invention additionally provides: a particulate composition which has dispersibility in an oil-based material; and a method for producing this particulate composition. A particulate composition according to the present invention contains solid particles and an amphiphilic substance that is present on the surfaces of the solid particles; and the amphiphilic substance has an ability of forming vesicles in water. A method for producing a particulate composition according to the present invention comprises: a step for preparing a mixture of solid particles and a solvent in which amphiphilic substance that has an ability of forming vesicles in water is dissolved; and a step for removing the solvent in the mixture.

9 Claims, 3 Drawing Sheets

(51) Int. Cl.
| | |
|---|---|
| *C09C 1/02* | (2006.01) |
| *C09C 1/24* | (2006.01) |
| *C09C 1/36* | (2006.01) |
| *C09C 3/06* | (2006.01) |
| *C09C 3/10* | (2006.01) |
| *C09D 5/02* | (2006.01) |
| *C09D 7/40* | (2018.01) |
| *C09D 7/62* | (2018.01) |
| *C09D 7/63* | (2018.01) |
| *C09D 17/00* | (2006.01) |
| *C09D 201/00* | (2006.01) |
| *C09K 23/00* | (2022.01) |

(56) References Cited

U.S. PATENT DOCUMENTS

| | | | | |
|---|---|---|---|---|
| 2007/0261293 | A1* | 11/2007 | Tajima | B01F 17/005 44/301 |
| 2009/0263660 | A1 | 10/2009 | Takeuchi et al. | |
| 2010/0003203 | A1* | 1/2010 | Karpov | A61K 8/27 424/59 |

FOREIGN PATENT DOCUMENTS

| | | |
|---|---|---|
| JP | 2006239666 A | 9/2006 |
| JP | 2008094656 A | 4/2008 |
| JP | 2011036760 A | 2/2011 |
| JP | 5155658 B2 | 3/2013 |
| WO | 2014157459 A1 | 10/2014 |

OTHER PUBLICATIONS

Kamiya et al.; Sci. Technol. Adv. Mater. (2010) 11; 7 pages; published Sep. 10, 2010.*

Akutsu, Masayuki et al., "Preparation of HCO-10 vesicle coated with functional fine particles"; Lecture abstracts of 56th panel discussion in Colloid and Surface Chemistry, CSJ, in particular, experiment operation, results and reviews, non-official, 2003, p. 173, 2D01.

Notice of Reasons for Rejection issued to JP Application No. 2018-562896, mailed Jun. 4, 2019.

International Search Report corresponding to Application No. PCT/JP2017/040635; Dated Dec. 12, 2017.

KIPO Office Action for corresponding KR Application No. 10-2019-7023659, Dated Dec. 24, 2020.

* cited by examiner

PARTICULATE COMPOSITION, LIQUID COMPOSITION, METHOD FOR PRODUCING PARTICULATE COMPOSITION, SURFACE MODIFYING AGENT, AND METHOD FOR IMPROVING WATER DISPERSIBILITY

CROSS REFERENCE TO RELATED APPLICATIONS

This is the U.S. national stage of application No. PCT/JP2017/040635, filed on Nov. 10, 2017. Priority under 35 U.S.C. § 119(a) and 35 U.S.C. § 365(b) is claimed from Japanese Application No. 2017-006136, filed Jan. 17, 2017; the disclosures of which are incorporated herein by reference.

TECHNICAL FIELD

The present invention relates to a particulate composition, a liquid composition, a method of manufacturing the particulate composition, a surface modifying agent and a method of improving water dispersibility.

BACKGROUND ART

Solid particles are used in many applications such as cosmetics and paints, and there is need for a technique for uniformly and stably dispersing the solid particles in a medium such as water. Particularly, UV particles or foundation pigment particles as a cosmetic agent and the like are required to have delicate stability under various dispersion conditions.

For example, Patent Document 1 discloses that subjecting surfaces of solid particles each containing a silicone resin and/or an organic powder to hydrophilization treatment with a water-soluble polyoxyalkylene glycol derivative, a water-soluble cationic polymer and a low-molecular weight organosilicone derivative improves water dispersibility.

Patent Document 1: Japanese Patent No. 5155658

DISCLOSURE OF THE INVENTION

Problems to be Solved by the Invention

However, in order to improve water dispersibility as in Patent Document 1, there is a problem that a hydrophilization treatment depending upon the type of solid particles (a silicone resin or the like) is necessary. Therefore, there is a need for a technique capable of enhancing water dispersibility regardless of the type of solid particles.

The present invention has been made in view of the above-mentioned circumstances, and an object of the present invention is to provide a particulate composition having a high water dispersibility regardless of the type of solid particles, and a method of producing the same. It is another object of the present invention to provide a method of improving a liquid composition, a surface modifying agent, and a method of improving water dispersibility. It is a further object of the present invention to provide a particulate composition having dispersibility in oily substances and a method of producing the same.

Means for Solving the Problems

The present inventors have found that coating the surface of solid particles with an amphiphilic substance capable of forming a vesicle in water increases the dispersibility of the solid particles in water or an oily substance, and thus have completed the present invention. More specifically, the present invention provides the following:

(1) A particulate composition, comprising solid particles and an amphiphilic substance present on a surface of the solid particles, wherein the amphiphilic substance is capable of forming a vesicle in water.

(2) The particulate composition according to (1), comprising an amphiphilic substance capable of coating a surface of the solid particles by forming six or more monolayers when the particulate composition is dispersed in water.

(3) The particulate composition according to (1) or (2), wherein a mean particle size when dispersed in water or an oily substance is 1.0 times or more and 1.5 times or less of a mean particle size when dispersed in ethanol.

(4) The particulate composition according to any one of (1) to (3), wherein the solid particles are particles of a metal oxide.

(5) A liquid composition comprising the particulate composition according to any one of (1) to (4) and water or an oily substance comprising the particulate composition.

(6) The liquid composition according to (5), wherein the solid particles are dispersed in the water with the surface of the solid particles being coated with six or more monolayers formed of the amphiphilic substance.

(7) The liquid composition according to (5) or (6), wherein the liquid composition is for cosmetics or paints.

(8) A method of producing the particulate composition according to any one of (1) to (4), comprising the steps of: preparing a mixture of solid particles and a solvent in which the amphiphilic substance capable of forming a vesicle in water is dissolved; and removing the solvent in the mixture.

(9) The method according to (8), wherein the solvent in the mixture is removed by vaporizing the solvent.

(10) A surface modifying agent for solid particles, wherein the surface modifying agent comprises an amphiphilic substance capable of forming a vesicle in water.

(11) A method of improving dispersibility of solid particles in water or an oily substance by covering a surface of the solid particles with an amphiphilic substance capable of forming a vesicle in water.

Effects of the Invention

It is an object of the present invention to provide a particulate composition having high water dispersibility regardless of the type of solid particles, and a method of producing the same. In addition, it is possible to provide a liquid composition, a surface modifying agent and a method of improving water dispersibility. Further, the present invention can provide a particulate composition having dispersibility in an oily substance and a method of producing the same.

PREFERRED MODE FOR CARRYING OUT THE INVENTION

Embodiments of the present invention are described below, but the present invention is not limited thereto.

<Particulate Compositions>

The present invention relates to a particulate composition comprising solid particles and an amphiphilic substance present on a surface of the solid particles, wherein the amphiphilic substance is capable of forming a vesicle in water. The invention thus has a high dispersibility in water or an oily substance, regardless of the type of solid particles. The reason is presumed to be as follows.

The amphiphilic substance of the present invention has the ability to form a vesicle in water, and the vesicle is known as a particle having so-called three-phase emulsifying ability. Particles of the vesicle, however, repel each other and a repulsive force is generated between the particles. Arranging such an amphiphilic substance on a surface of solid particles is presumed to generate repulsive force between the solid particles, resulting in improvement in dispersibility in water or an oily substance. Particularly, it is inferred that: the amphiphilic substance forms a multilayer film on the surface of the solid particles, thereby a repulsive force exceeding the attractive force is easily generated between the solid particles, and this prevents the solid particles from aggregating in water or an oily substance, so that improvement in dispersibility is achieved. It should be noted that even if the amphiphilic substance, which functions as a coating agent, is present in excess in the present particulate composition, when the particulate composition is dispersed in water, the excess amphiphilic substance forms a vesicle due to its self-assembling ability and is dispersed; therefore, the excess amphiphilic substance does not hinder the solid particles from being dispersed. In addition, when the particulate composition is dispersed in an oily substance, the amphiphilic substance itself is not dissolved in the oil substance, so that the solid particles are not hindered from being dispersed.

It should be noted that in the three-phase emulsification method, the vesicle formed by the amphiphilic substance capable of forming a vesicle in water exists at an oil-water interface and adsorbs to the oil phase through van der Waals force, so that emulsification is achieved. The three-phase emulsification mechanism is quite different from the emulsification mechanism in which the interfacial tension between oil and water is reduced by the orientation of the aqueous portion and the hydrophobic portion in the aqueous phase and the oil phase, respectively. (see, for example, Japanese Patent No. 3855203). Although the vesicle in water does not emulsify solid particles in the present invention, it has been found that use of an amphiphilic substance that forms a vesicle in water (i.e., capable of forming a three-phase emulsion) as a coating agent in the present invention results in an increase in dispersibility of the surface of solid particles in water or an oily substance. Whether or not a particular particle is a particle that can be used for three-phase emulsification can be determined by light scattering measurement of this hydrophilic nanoparticle dispersion, and confirming that the mean particle size is, for example, 8 to 400 nm. It can be determined by further performing atomic force microscopy (AFM) observation of the prepared emulsion and confirming that particles of the emulsifying agent adhere to a surface of oil droplets.

(Amphiphilic Substances)

The amphiphilic substance used in the present invention is an amphiphilic substance capable of forming a vesicle in water (hereinafter, sometimes abbreviated as "amphiphilic substance") and is, for example, capable of forming a bilayer in water (i.e., capable of forming a vesicle in water). As such an amphiphilic substance capable of forming a bilayer in water, it is preferable to employ a derivative of polyoxyethylene-hydrogenated castor oil represented by the following general formula 1 or a derivative of a halogen salt of a dialkylammonium derivative, a trialkylammonium derivative, a tetraalkylammonium derivative, a dialkenylammonium derivative, a trialkenylammonium derivative, or a tetraalkenylammonium derivative as represented by the general formula 2.

General Formula 1

[Chem. 1]

$$E = 1 + M + N + X + Y + Z$$

As the amphiphilic substance capable of forming a bilayer in water, derivatives of polyoxyethylene-hydrogenated castor oil (HCO-10, HCO-20, HCO-30, HCO-40, HCO-50, HCO-100 or the like manufactured by Nikko Chemicals Co., Ltd.) are preferable.

General Formula 2

[Chem. 2]

wherein $R_1$ and $R_2$ are each independently an alkyl group or alkenyl group having 8 to 22 carbon atoms, $R_3$ and $R_4$ are each independently hydrogen or an alkyl group having 1 to 4 carbon atoms, and X is F, Cl, Br, I or $CH_3COO$.

Alternatively, a phospholipid, a phospholipid derivative or the like may be employed as the amphiphilic substance capable of forming a bilayer in water. As the phospholipid, among the constituents represented by the following general formula 3, DLPC (1, 2-dilauroyl-sn-glycero-3-phospho-rac-1-choline) having a carbon chain length of 12, DMPC (1, 2-dimyristoyl-sn-glycero-3-phospho-rac-1-choline) having a carbon chain length of 14 and DPPC (1, 2-dipalmitoyl-sn-glycero-3-phospho-rac-1-choline) having a carbon chain length of 16 can be employed.

General Formula 3

[Chem. 3]

In addition, in the configurations represented by the following general formula 4, a Na salt or an NH$_4$ salt of DLPG (1, 2-dilauroyl-sn-glycero-3-phospho-rac-1-glycerol) having a carbon chain length of 12, a Na salt or an NH$_4$ salt of DMPG (1,2-dimyristoyl-sn-glycero-3-phospho-rac-1-glycerol) having a carbon chain length of 14 and a Na salt or an NH$_4$ salt of DPPG (1,2-dipalmitoyl-sn-glycero-3-phospho-rac-1-glycerol) having a carbon chain length of 16 may be employed.

General Formula 4

[Chem. 4]

As the phospholipid or the phospholipid derivative, lecithin (natural lecithin, hydrogenated lecithin or the like) can be used.

Fatty acid esters may be employed as the amphiphilic substance capable of forming a bilayer in water. As the fatty acid ester, for example, glycerin fatty acid esters (tetraglyceryl monostearate, decaglyceryl tristearate or the like), sucrose fatty acid esters (sucrose stearate or the like), sorbitan fatty acid esters, propylene glycol fatty acid esters or the like can be used. Of these, the glycerin fatty acid ester and the sucrose fatty acid ester are particularly preferable.

As described below, when the solid particles are dispersed in water, it is desirable that the surface of the solid particles be coated with six or more monolayers formed of the amphiphilic substance (three or more bilayers). That is, it is preferable that the amphiphilic substance of the present invention is capable of forming six or more monolayers and covering the surface of the solid particles. This is technical knowledge found by the present inventors. Therefore, ideally, if the amphiphilic substance is contained in an amount sufficient for forming six monolayers, the dispersibility of the solid particles in water can be considered to be ensured. However, even if the amphiphilic substance is present in excess, the excess amphiphilic substance forms a vesicle due to its self-assembling ability and is dispersed in water as described above. Therefore, the excess amphiphilic substance does not hinder the solid particles from being dispersed. On the other hand, when dispersed in an oily substance, the amphiphilic substance does not form a layer but covers the solid particles. As described above, the solid particles covered with the amphiphilic substance are dispersed in the oily substance due to the action of wetting with the oily substance. Even if the amphiphilic substance is added in excess, the excess amphiphilic substance does not dissolve in the oily substance, so that the excess amphiphilic substance does not hinder the solid particles from being dispersed.

Examples of the solid particles used in the particulate composition of the present invention include, for example, inorganic particles such as metals, metal oxides, metal sulfides, complex salts thereof, and organic particles. Examples of the metal oxide include titanium oxide, cerium oxide, iron oxide (iron tetraoxide, iron dioxide, iron trioxide and the like), zinc oxide, silicon oxide and the like. Examples of the organic particles include carbon fine particles, polystyrene, polyacrylic acid esters, polyvinyl acetate and the like. Among these, the metal oxide is preferable as the solid particle.

The solid particles may be those subjected to surface treatment (e.g., hydrophilization treatment or hydrophobization treatment) in advance with a substance different from the amphiphilic substance or may be those not subjected to surface treatment. The solid particles are useful also in that, regardless of the state of the surface, high dispersibility in water or an oily substance can be obtained by surface treatment with an amphiphilic substance.

Since the particulate composition of the present invention has high dispersibility in water or an oily substance as described above and aggregation among the solid particles is suppressed, a mean particle size of the solid particles of the present invention is smaller than the mean particle size of the solid particles before being subjected to coating treatment (i.e., the solid particles which do not have any amphiphilic substance on the surface), when dispersed in water or an oily substance. In particular, it is preferable that the mean particle size of the particulate composition of the present invention when dispersed in water or an oily substance is equal to the mean particle size obtained when the solid particles, before being subjected to coating treatment, are dispersed in ethanol. Specifically, the mean particle size of the particulate composition of the present invention obtained when dispersed in water or an oily substance is preferably 1.5 times or less, more preferably 1.4 times or less, still more preferably 1.3 times or less, and particularly preferably 1.2 times or less, relative to the mean particle size obtained when the solid particles, before being subjected to coating treatment, are dispersed in ethanol. Additionally, the mean particle size of the present particulate composition obtained when dispersed in water or an oily substance may be 1.0 time or more (1.01 times or more, 1.05 times or more, 1.1 times or more or the like), relative to the mean particle size obtained when the solid particles, before being subjected to coating treatment, are dispersed in ethanol. The mean particle size of the particulate composition of the present invention when dispersed in water or an oily substance is measured in water or an oily substance, using a dynamic/electrophoretic light scattering photometer (ELSZ, manufactured by Otsuka Electronics Co., Ltd.). It should be noted that the mean particle size of the uncoated solid particles dispersed in ethanol is also measured using a dynamic/electrophoretic light scattering photometer (ELSZ, manufactured by Otsuka Electronics Co., Ltd.), as they are. The measured value of the mean particle size by using the dynamic/electrophoretic light scattering photometer (ELSZ, manufactured by Otsuka Electronics Co., Ltd.) is a value calculated and outputted by assuming that all the particles are spherical in the measuring device.

In the present invention, it is considered that a higher dispersibility of the solid particles in water or an oily substance can be obtained if six layers (three bilayers) are established as the number of monolayers formed of the amphiphilic substance covering the solid particles. The number of layers of the amphiphilic substance covering the solid particles can be expressed by the coating ratio ($\varphi$) calculated according to the formula (14) described below. Here, the method of calculating equation (14) is described below. In the description of the present specification, the term "coating agent" is synonymous with the term "amphiphilic substance capable of forming a vesicle in water or in an oily substance" used in the present invention.

The mass of the solid particles to be treated is defined as $m_S$ [g]. First, the total surface area (S [nm$^2$]) of the solid particles is represented by the following equation (1).

[Math. 1]

$$S = s \times N_S \tag{1}$$

S: Total surface area of the solid particles in an amount of $m_s$, a mass of the solid particles [nm$^2$]
s: Total surface area (average) per solid particle [nm$^2$]
$N_S$: Number of solid particles The surface area per solid particle (s [nm$^2$]) in equation (1) can be represented by the following equation (2).

[Math. 2]

$$s = 4 \times \pi \times \left(\frac{D}{2}\right)^2 \tag{2}$$
$$= \pi \times D^2$$

D: Mean particle size of the solid particles when dispersed in 99.5% ethanol
$\pi$: Circle ratio (3.14)

The number of the solid particles ($N_S$) in equation (1) can be expressed by the following equation (3).

[Math. 3]

$$N_S = \frac{V_S}{v_S} \tag{3}$$

$V_S$: Total volume of the solid particles [nm$^3$]
$v_S$: Volume (average) per solid particle [nm$^3$]

The total volume ($V_S$ [nm$^3$]) of the solid particles and the volume ($v_S$ [nm$^3$]) per solid particle in equation (3) can be expressed by the following equations (4) and (5), respectively.

[Math. 4]

$$V_S = \frac{m_S \times 10^{21}}{d_S \times \theta} \tag{4}$$

$m_S$: Mass of the solid particles [g]
$d_S$: Specific gravity of the solid particles [g/cm$^3$]
$\theta$: Close packing ratio (0.74)

[Math. 5]

$$v_S = \frac{4}{3} \times \pi \times \left(\frac{D}{2}\right)^3 \tag{5}$$
$$= \frac{\pi \times D^3}{6}$$

Equation (3) can be converted into equation (6) below by substituting equations (4) and (5) into equation (3).

[Math. 6]

$$N_S = \frac{6 \times 10^{21} \times m_S}{\theta \times \pi \times d_S \times D^3} \tag{6}$$

The total surface area (S [nm$^2$]) of the solid particles represented by equation (1) can be converted into the following equation (7) by substituting equation (2) and equation (6) into equation (1).

[Math. 7]

$$S = \frac{6 \times 10^{21} \times m_S}{\theta \times d_S \times D} \tag{7}$$

The total area (P [nm$^2$]) of cross sections of molecules of the coating agent can be expressed by the following equation (8) by assuming that each molecule of the coating agent for coating the solid particles is a sphere and defining the mass of the coating agent as $m_C$ [g].

[Math. 8]

$$P = p \times N_C \tag{8}$$

P: Total cross section area of the coating agent coating the solid particles [nm²]
p: Cross-section area per molecule of the coating agent coating the solid particles [nm²]
$N_C$: Number of molecules of the coating agent The volume ($v_C$ [nm³]) per molecule of the coating agent used for coating can be expressed by the following equation (9).

[Math. 9]

$$v_C = \frac{M \times 10^{21}}{N_A \times d_C} \tag{9}$$

M: Molecular weight of the coating agent [g/mol]
$N_A$: Avogadro constant (6.022×10²³) [the number of molecules/mol]
$d_C$: Specific gravity of the coating agent [g/cm³]

Upon using equation (9), the radius (r [nm]) per molecule of the coating agent used for coating can be expressed by the following equation (10).

[Math. 10]

$$r = \left(\frac{3 \times 10^{21} \times M}{4 \times \pi \times N_A \times d_C}\right)^{\frac{1}{3}} \tag{10}$$

Upon using equation (10), the cross sectional area (p [nm²]) per molecule of the coating agent for coating the solid particles in equation (8) can be represented by the following equation (11).

[Math. 11]

$$p = \pi \times r^2 \tag{11}$$
$$= \left(\frac{3 \times M}{4 \times N_A \times d_C}\right)^{\frac{2}{3}} \times \pi^{\frac{1}{3}} \times 10^{14}$$

The number ($N_C$) of molecules of the coating agent in equation (8) can be represented by the following equation (12).

[Math. 12]

$$N_C = \frac{N_A \times m_C}{M} \tag{12}$$

$m_C$: Mass of the coating agent

Equation (8) can be converted into equation (13) below by substituting equations (11) and (12) into equation (8).

[Math. 13]

$$P = \frac{3^{\frac{2}{3}} \times 10^{14} \times \pi^{\frac{1}{3}} \times N_A^{\frac{1}{3}} \times m_C}{4^{\frac{2}{3}} \times d_C^{\frac{2}{3}} \times M^{\frac{1}{3}}} \tag{13}$$

The coating ratio (φ) of the coating agent with respect to the solid particles can be expressed by dividing the total cross-sectional area (P [nm²]) of the molecules of the coating agent by the total surface area (S [nm²]) of the solid particles. Here, the coating ratio (φ) represents the number of monolayers formed on the surface of the solid particles by the coating agent, as described above. Therefore, using (5) represented by equation (7) and (P) represented by equation (13) allows the coating ratio (φ) of the coating agent with respect to the solid particles to be represented by equation (14) below.

[Math. 14]

$$\phi = \frac{P}{S} \tag{14}$$
$$= 1.38 \times 10^{-8} \times \frac{\pi^3 \times N_A^{\frac{1}{3}} \times m_C \times \theta \times d_S \times D}{d_C^{\frac{2}{3}} \times M^{\frac{1}{3}} \times m_S} \times \pi^{\frac{1}{3}} \times 10^{14}$$

Since π, θ, and $N_A$ are constants, once the type of the coating agent is determined, the molecular weight and specific gravity of the coating agent are determined. Once the type of the solid particles is determined, the specific gravity of the solid particles is determined. Therefore, the coating ratio can be adjusted by determining the type of coating agents and the type of solid particles; substituting the molecular weight and the specific gravity of the coating agent, as well as the specific gravity of the solid particles and the mean particle size in ethanol of the solid particles; and, based on the values obtained, adjusting the mass of the coating agent and the mass of the solid particles. The mean particle size (D) of the solid particles when dispersed in ethanol is measured using the dynamic/electrophoretic light scattering photometer (ELSZ, manufactured by Otsuka Electronics Co., Ltd.), as they are.

In the present particulate composition, the coating ratio (φ) of the coating agent with respect to the solid particles is preferably 6 or more, preferably 8 or more, and preferably 10 or more. The upper limit of the coating ratio (φ) is not particularly limited, and may be, for example, 50 or less. As described below in the Examples, the number of layers of the coating agent needs to be six when counted in monolayers (three when counted in bilayers) by TEM-observation in order to ensure the dispersion state of the solid particles.

In addition, the mass ($m_C$ [g]) of the vesicle required to achieve the coating ratio (φ) of six or more can be represented by the following equation (15) using equation (14).

[Math. 15]

$$m_C \geq 4.36 \times 10^8 \frac{d_C^{\frac{2}{3}} \times M^{\frac{1}{3}} \times m_S}{\pi^{\frac{1}{3}} \times N_A^{\frac{1}{3}} \times \theta \times d_S \times D} \tag{15}$$

Further, equation (15) can be converted into equation (16) by substituting the values of the constants of $\pi$, $\theta$ and $N_A$ into equation (15).

[Math. 16]

$$m_C \geq 4.77 \times \frac{d_C^3 \times M^{\frac{2}{3}} \times m_S}{d_S \times D} \quad (16)$$

Therefore, in order that the present particulate composition has high dispersibility in water or an oily substance, it is preferable that the mass ($m_C$ [g]) of the coating agent for coating the solid particles satisfies equation (16).

(Oily Substances)

The oily substance is not particularly limited as long as the solubility of the amphiphilic substance is high (specifically, 1 µmol/L or more), and either a nonpolar solvent or a polar solvent can be used. Specific examples of the nonpolar solvent include hydrocarbon oils such as straight chain paraffins, branched chain paraffins, alicyclic hydrocarbons, and the like. Examples of the polar solvent include ester oils, silicone oils and fatty acid triglycerides, and the like.

The oily substance may be a substance in a solid state at an ambient temperature, in addition to a substance in a liquid state at an ambient temperature. An oily substance, which is solid at an ambient temperature, may also be used if it has fluidity in a dispersed state, for instance, when heated.

Depending on the purpose of the present invention, components other than the solid particles and the coating agent may or may not be blended.

<Production Methods of Particulate Compositions>

The present invention also encompasses a method of producing the particulate composition described above. The inventive particulate composition can be produced, for example, by the following methods. That is, the particulate composition can be produced by a method comprising the steps of preparing a mixture of solid particles and a solvent in which an amphiphilic substance capable of forming a vesicle in water is dissolved; and removing the solvent in the mixture.

(Preparation Step)

The preparation step in the present invention is a step of preparing a mixture of solid particles and a solvent in which an amphiphilic substance capable of forming a vesicle in water is dissolved.

As the solid particles and the amphiphilic substance, those described above can be used.

Any solvent can be used as long as it can dissolve the amphiphilic substance to be used, and can be selected depending upon the type of the amphiphilic substance. Examples of solvents that can be used include volatile or removable organic solvents such as methanol, ethanol, isopropyl alcohol, acetone, chloroform, tetrahydrofuran, ethyl acetate, butyl acetate and short chain hydrocarbons. A "solvent for an amphiphilic substance" means a solvent capable of dissolving 0.01 g or more of the amphiphilic substance in 1 mL of the solvent at 20° C.

The mixture may be prepared in any manner, for example, by adding the solid particles and the amphiphilic substance to a solvent, followed by stirring.

(Removing Step)

The removing step in the present invention is a step of removing the solvent in the mixture prepared in the preparing step.

The method of removing the solvent in the mixture is not particularly limited, but is preferably performed by vaporizing the solvent. The method of vaporizing a solvent is not particularly limited, and for example, the solvent in the mixture may be removed by drying using a dryer.

The manufacturing method of the present invention may or may not include steps other than the above-described preparation step and removing step. For example, the method may further include a step of dispersing the particulate composition obtained after the removing step in water or an oily substance to confirm dispersibility. Dispersibility can be confirmed by measuring the mean particle size of the particulate composition and the mean particle size of solid particles to which no amphiphilic substance is formulated, and confirming that the mean particle size of the particulate composition is smaller.

<Liquid Composition>

The present invention encompasses a liquid composition having the particulate composition of the invention described above and water or an oily substance comprising the particulate composition.

The liquid composition of the present invention can be produced by dispersing the above-mentioned particulate composition in water or in an oily substance.

The amount of the particulate composition of the present invention is not particularly limited, and may be appropriately selected depending upon the purpose and dispersibility. The amount of the inventive particulate composition may be, for example, 0.1 mg to 70 g relative to 100 ml of the water or the oily substance.

The applications of the liquid composition of the present invention are not particularly limited, but it is preferably used for cosmetics, paints, lubricants, solid agricultural chemicals, abrasives, printing inks, paper making, chemical fibers, rubbers, coloring materials, crayons, ceramics, electronic materials, catalysts, adhesives, glazes, pharmaceuticals, construction civil engineering materials and the like.

Since the inventive particulate composition is highly dispersible in water or an oily substance, the composition is suitable for use in which the particulate composition is dispersed in water or an oily substance and used (i.e., for the above-mentioned applications of the liquid composition). The inventive particulate composition may also be, however, dispersed in solids, for example in plastics.

The inventive liquid composition may or may not have components other than the particulate composition in water or an oily substance. The components other than the particulate composition in water or an oily substance can be selected, for example, depending on the application.

The inventive liquid composition may be a liquid composition packed in a container or may be a liquid composition itself not packed in a container.

<Surface Modifying Agent>

The present invention encompasses a surface modifying agent for solid particles, wherein the surface modifying agent comprises an amphiphilic substance capable of forming a vesicle in water.

In the present invention, the term "surface modifying" refers to an application for improving dispersibility of solid particles in water or an oily substance by formulating, for example, to a surface of the solid particles.

For the solid particles and the amphiphilic substance of the present invention, the solid particles and the amphiphilic substance which are the same as those contained in the above-mentioned particulate composition can be used.

<Method of Improving Dispersibility in Water or an Oily Substance>

The present invention encompasses a method of improving dispersibility of solid particles in water or an oily substance by covering a surface of the solid particles with an amphiphilic substance capable of forming a vesicle in water. This improves dispersibility of the solid particles in water or an oily substance.

The method of coating a surface of solid particles with an amphiphilic substance capable of forming a vesicle in water can be performed, for example, by adding the amphiphilic substance and the solid particles to a solvent for the amphiphilic substance and then removing the solvent, for instance, by drying.

For the solid particles and the amphiphilic substance of the present invention, the solid particles and the amphiphilic substance which are the same as those contained in the above-mentioned particulate composition can be used.

EXAMPLES

Examples 1 to 5

The particulate compositions of Example 1 to 5 were prepared in the formulations of Tables 1 and 2 described below. Specifically, first, an organic solvent solution of polyoxyethylene-hydrogenated castor oil derivative (HCO-40) was prepared. The solution of amphiphilic substance capable of forming a vesicle of this polyoxyethylene-hydrogenated castor oil derivative (HCO-40), and solid particles (untreated cerium oxide having a broad particle size distribution (hereinafter referred to as "cerium oxide A"), cerium oxide A with its surface treated with silica, cerium oxide A with its surface treated with stearic acid, untreated cerium oxide having narrow particle size distribution (hereinafter referred to as "cerium oxide B") or cerium oxide B with its surface treated with stearic acid ("AQUACERIA Powder S" manufactured by Approse Corporation)) were added to ethanol as an organic solvent, stirred, and agitated using a stirrer for 2 to 3 hours. The obtained mixture was then heated while being stirred with a hot stirrer to vaporize the solvent. Then, the mixture was dried in a dryer at 80° C. for 2 to 3 hours to completely remove the solvent, and the particulate compositions of Examples 1 to 5 were prepared.

Reference Example 1 and Comparative Examples 1 to 5

Solid particles were provided in amounts indicated in Tables 1 and 2 below and used as the particles of Reference Example 1 and Comparative Examples 1 to 5.

<Evaluation of Water Dispersibility 1>

The particulate compositions of Examples 1 to 5 and the particles of Comparative Examples 1 to 5 were dispersed in water, and the mean particle size of each of the above was measured using a dynamic/electrophoretic light scattering photometer (ELSZ, manufactured by Otsuka Electronics Co., Ltd.). Measurement was performed after preparing a solid particle dispersion by adding water to each of the particulate compositions or particles in a dried state so that the total weight is 10.0 g and a solid particle dispersion of 20 wt % is formed, followed by further dilution with water. In addition, the particles of Reference Example 1 were dispersed in ethanol, and the mean particle size was measured using a dynamic/electrophoretic light scattering photometer (ELSZ, manufactured by Otsuka Electronics Co., Ltd.). Dispersibility of the particulate compositions of each of the Examples and the particles of the Reference Example and each of the Comparative Examples was evaluated based on comparison with dispersibility of a corresponding Comparative Example in which treatment using the polyoxyethylene-hydrogenated castor oil derivative (HCO-40) as the amphiphilic substance capable of forming a vesicle was not performed (for instance, based on comparison of Example 1 with Comparative Example 1): when the particle size of Example 1 was smaller than that of Comparative Example 1 and powder floating was not observed, the water dispersibility of Example 1 was evaluated as "++" (good). Poor water dispersibility was evaluated as "−" (bad). The results are indicated in Tables 1 and 2 below.

TABLE 1

| Components | Reference Example 1 | Comparative Example 1 | Example 1 | Comparative Example 2 | Example 2 | Comparative Example 3 |
|---|---|---|---|---|---|---|
| Cerium oxide A (untreated) | 2 g | 2 g | 2 g | − | − | − |
| Cerium oxide A (silica-treated) | − | − | − | 2 g | 2 g | − |
| Cerium oxide A (stearic acid-treated) | − | − | − | − | − | 2 g |
| Cerium oxide B (untreated) | − | − | − | − | − | − |
| Cerium oxide B (stearic acid-treated) | − | − | − | − | − | − |
| HCO-40 | − | − | 0.1 g | − | 0.1 g | − |
| Mean particle size in water dispersion (nm) | − | 551.3 | 350 | 532.8 | 365.3 | Powder floating |
| Mean particle size in ethanol dispersion (nm) | 350 | − | − | − | − | − |
| Evaluation of water dispersibility | − | − | ++ | − | ++ | − |

TABLE 2

| Components | Example 3 | Comparative Example 4 | Example 4 | Comparative Example 5 | Example 5 |
| --- | --- | --- | --- | --- | --- |
| Cerium oxide A (untreated) | — | — | — | — | — |
| Cerium oxide A (silica-treated) | — | — | — | — | — |
| Cerium oxide A (stearic acid-treated) | 2 g | — | — | — | — |
| Cerium oxide B (untreated) | — | 2 g | 2 g | — | — |
| Cerium oxide B (stearic acid-treated) | — | — | — | 2 g | 2 g |
| HCO-40 | 0.1 g | — | 0.1 g | — | 0.1 g |
| Mean particle size in water dispersion (nm) | 370.7 | 2667.9 | 595.1 | Powder floating | 305.5 |
| Mean particle size in ethanol dispersion (nm) | — | — | — | — | — |
| Evaluation of water dispersibility | ++ | — | ++ | — | ++ |

As indicated in Tables 1 and 2, regardless of the surface treatment of the solid particles and the particle size distribution width, the particle size of the solid particles with its surface treated with an amphiphilic substance capable of forming a vesicle in water was small. The water dispersibility in all of the Examples was confirmed to be improved compared to the Comparative Examples. In addition, for example, as can be seen from comparison of Example 1 and Reference Example 1, it was found that treating a surface of the solid particles with an amphiphilic substance results in almost the same mean particle size obtained when the solid particles are dispersed in ethanol (namely, a state in which particles are more easily dispersed than in water).

Examples 6 and 7 and Comparative Examples 6 and 7

The particulate compositions of Examples 6 and 7 were prepared according to the formulations provided in Table 3 below. Specifically, the particulate compositions of Examples 6 and 7 were prepared in the same manner as in Example 1 except that cerium oxide A (untreated) and cerium oxide B (untreated) were changed to untreated zinc oxide having a broad particle size distribution width (hereinafter referred to as "zinc oxide A") and untreated zinc oxide having a narrow particle size distribution width (hereinafter referred to as "zinc oxide B"), respectively. In addition, solid particles were provided in amounts indicated in Table 3 below and used as the particles of Comparative Examples 6 and 7.

<Evaluation of Water Dispersibility 2>

The particulate compositions of Examples 6 and 7 and the particles of Comparative Examples 6 to 7 were dispersed in water, and the mean particle sizes were measured using a dynamic-electrophoretic light scattering photometer (ELSZ, manufactured by Otsuka Electronics Co., Ltd.). The measurement was performed in the same manner as in the above-mentioned "Evaluation of Water Dispersibility 1". In addition, the water dispersibility of each of the particulate compositions of the Examples and that of the particles of the Comparative Example were evaluated based on the same criteria as that of the above-mentioned "Evaluation of Water Dispersibility 1". The results are presented in the following Table 3.

TABLE 3

| Components | Comparative Example 6 | Example 6 | Comparative Example 7 | Example 7 |
| --- | --- | --- | --- | --- |
| Zinc oxide A (untreated) | 2 g | 2 g | — | — |
| Zinc oxide B (untreated) | — | — | 2 g | 2 g |
| HCO-40 | — | 0.1 g | — | 0.1 g |
| Mean particle size in water dispersion (nm) | 4032.9 | 1219.7 | 4287.6 | 1612.8 |
| Evaluation of water dispersibility | — | ++ | — | ++ |

As indicated in Table 3, it was found that also in using zinc oxide, high water dispersibility can be obtained by surface treating the solid particles with the amphiphilic substance capable of forming a vesicle in water, as in using cerium oxide.

Examples 8 to 11 and Comparative Example 8

The particulate compositions of Examples 8 to 11 were prepared according to the formulations provided in Table 4 below. Specifically, the particulate composition of Example 8 was prepared in the same manner as in Example 1 except that cerium oxide A (untreated) was changed to silicon oxide (Aerosil OX 50 manufactured by Nippon Aerosil Co., Ltd.) and the formulation amount was changed as indicated in Table 4. The particulate compositions of Examples 9 to 11 were prepared in the same manner as in Example 1 except that cerium oxide A (untreated) was changed to silicon oxide (Aerosil OX 50 manufactured by Nippon Aerosil Co., Ltd.), the formulation amounts were changed as indicated in Table 4, and the organic solvent used for the preparation was changed from ethanol to acetone, chloroform, or isopropyl alcohol (IPA), respectively. In addition, solid particles were provided in an amount indicated in Table 4 described below, and were used as the particles of Comparative Example 8.

<Evaluation of Water Dispersibility 3>

The particulate compositions of Examples 8 to 11 and the particles of Comparative Example 8 were dispersed in water, and the mean particle sizes were measured using a dynamic-electrophoretic light scattering photometer (ELSZ, manufactured by Otsuka Electronics Co., Ltd.). The measurement was performed in the same manner as in the above-mentioned "Evaluation of Water Dispersibility 1". In addition, the water dispersibility of each of the particulate compositions of the Examples and that of the particles of the Comparative Example were evaluated based on the same criteria as that of the above-mentioned "Evaluation of Water Dispersibility 1". The results are presented in the following Table 4.

TABLE 4

| Components | Comparative Example 8 | Example 8 | Example 9 | Example 10 | Example 11 |
|---|---|---|---|---|---|
| Silicon oxide | 0.03 g | 0.03 g | 0.03 g | 0.03 g | 0.03 g |
| HCO-40 | — | 0.03 g | 0.03 g | 0.03 g | 0.03 g |
| Organic solvent | — | Ethanol | Acetone | Chloroform | IPA |
| Mean particle size in water dispersion (nm) | 773.9 | 280 | 271 | 183 | 330 |
| Evaluation of water dispersibility | — | ++ | ++ | ++ | ++ |

As indicated in Table 4, it was found that even if the type of solvents used for the preparation of the particulate composition was changed, high water dispersibility could be obtained by surface treating the solid particles with the amphiphilic substance capable of forming a vesicle in water.

Examples 12 to 18

The particulate compositions of Examples 12 to 18 were prepared according to the formulations of Tables 5 below. Specifically, the particulate compositions of Examples 12 to 18 were prepared in the same manner as in Example 5 except that the formulation amount of polyoxyethylene-hydrogenated castor oil derivative (HCO-40) as the amphiphilic substance capable of forming a vesicle was changed as indicated in Table 5.

<Evaluation of Water Dispersibility 4>

The particulate compositions of Examples 12 to 18 and the particles of Comparative Example 5 were dispersed in water, and the mean particle sizes were measured using a dynamic-electrophoretic light scattering photometer (ELSZ, manufactured by Otsuka Electronics Co., Ltd.). The measurement was performed in the same manner as in the above-mentioned "Evaluation of Water Dispersibility 1". In addition, the water dispersibility of each of the particulate compositions of the Examples and that of the particles of the Comparative Example were evaluated based on the same criteria as that of the above-mentioned "Evaluation of Water Dispersibility 1". The results are presented in the following Table 5. With respect to the item for evaluation of water dispersibility, "+" represents being slightly good.

TABLE 5

| Components | Comparative Example 5 | Example 12 | Example 13 | Example 14 | Example 15 | Example 16 | Example 17 | Example 18 |
|---|---|---|---|---|---|---|---|---|
| Cerium oxide B (stearic acid-treated) | 2 g | 2 g | 2 g | 2 g | 2 g | 2 g | 2 g | 2 g |
| HCO-40 | – | 0.05 g | 0.06 g | 0.1 g | 0.15 g | 0.2 g | 0.25 g | 0.3 g |
| Mean particle size in water dispersion (nm) | – | 4331.1 | 502 | 473 | 517.3 | 403.7 | 378.6 | 375.1 |
| Evaluation of water dispersibility | – | + (Powder floating) | ++ | ++ | ++ | ++ | ++ | ++ |
| Coating ratio ($\varphi$) | 0 | 5.5 | 6.5 | 11 | 16.5 | 22 | 27.5 | 33 |
| Weight ratio of HCO-40 to $CeO_2$ (wt %) | 0 | 2.5 | 3 | 5 | 7.5 | 10 | 12.5 | 15 |

As indicated in Table 5, it was found that when amount ratio of the amphiphilic substance to the cerium oxide was equal to a particular value (i.e., the coating ratio φ is 6) or more, the mean particle size of the particulate composition in water decreased, in other words, dispersibility in water increased.

Examples 19 to 24, Comparative Examples 9 to 10 and Reference Examples 2 to 3

The particulate compositions of Examples 19 to 24 were prepared according to the formulations provided in Tables 6 and 7 described below. Specifically, the particulate compositions of Examples 19 to 24 were prepared in the same manner as in Example 1, except that cerium oxide A (untreated) was replaced with iron oxide (methicone-treated) (SI-2 Tarox LLXLO) or titanium oxide (Al, stearic acid-treated) (MT-100Z manufactured by Tayca Co., Ltd.) and the formulation amounts of polyoxyethylene-hydrogenated castor oil derivative (HCO-40) as the amphiphilic substance capable of forming a vesicle were changed as indicated in Tables 6 and 7. In addition, solid particles were provided in amounts indicated in Tables 6 and 7 described below, and were used as the particles of Reference Examples 2 and 3 and Comparative Examples 9 to 10.

<Evaluation of Water Dispersibility 5>

The particulate compositions of Examples 19 to 24, the particles of Comparative Examples 9 to 10 and Reference Examples 2 to 3 were dispersed in water, and the mean particle sizes were measured using a dynamic-electrophoretic light scattering photometer (ELSZ, manufactured by Otsuka Electronics Co., Ltd.). The measurement was performed in the same manner as in the above-mentioned "Evaluation of Water Dispersibility 1". In addition, the water dispersibility of each of the particulate compositions of the Examples and that of the particles of the Comparative Example were evaluated based on the same criteria as that of the above-mentioned "Evaluation of Water Dispersibility 1". The results are indicated in Tables 6 and 7 below.

TABLE 6

| Components | Reference Example 2 | Comparative Example 9 | Example 19 | Example 20 | Reference Example 3 |
|---|---|---|---|---|---|
| Iron oxide (Methicone-treated) | 2 g | 2 g | 2 g | 2 g | — |
| Titanium dioxide (Al, stearic acid-treated) | — | — | — | — | 2 g |
| HCO-40 | — | — | 0.2 g | 0.3 g | 0.1 g |
| Mean particle size in water dispersion (nm) | — | — | 724.3 | 863.3 | — |
| Mean particle size in ethanol dispersion (nm) | 611.2 | — | — | — | 383.4 |
| Evaluation of water dispersibility | — | (Powder floating) | ++ | ++ | — |
| Weight ratio of HCO-40 to solid particles (wt %) | 0 | 0 | 10 | 15 | 2.5 |

TABLE 7

| Components | Comparative Example 10 | Example 21 | Example 22 | Example 23 | Example 24 |
|---|---|---|---|---|---|
| Iron oxide (Methicone-treated) | — | — | — | — | — |
| Titanium dioxide (Al, stearic acid-treated) | 2 g | 2 g | 2 g | 2 g | 2 g |
| HCO-40 | — | 0.3 g | 0.5 g | 0.8 g | 1.2 g |
| Mean particle size in water dispersion (nm) | — | 1076.4 | 472.9 | 435.7 | 430 |
| Mean particle size in ethanol dispersion (nm) | — | — | — | — | — |
| Evaluation of water dispersibility | (Powder floating) | ++ | ++ | ++ | ++ |
| Weight ratio of HCO-40 to solid particles (wt %) | 5 | 15 | 25 | 40 | 60 |

As indicated in Tables 6 and 7, it was found that even if the solid particles were changed to iron oxide (methicone-treated) or titanium oxide (Al, stearic acid-treated), high water dispersibility could be obtained by surface treating the solid particles with the amphiphilic substance capable of forming a vesicle in water. It was also found that, likewise to cerium oxide, when solid particles of iron oxide (methicone-treated) and titanium oxide (Al, stearic acid treated) were used and the amount of the amphiphilic substance relative to that of the solid particles was equal to a particular value or more, the mean particle size of the particulate composition in water decreased, in other words, dispersibility in water increased.

Examples 25 to 30

The particulate compositions of Examples 25 to 30 were prepared according to the formulations of Tables 8 and 9 described below. Specifically, the particulate compositions of Examples 25 to 30 were prepared in the same manner as in Example 1, except that the polyoxyethylene-hydrogenated castor oil derivative (HCO-40) as the amphiphilic substance capable of forming a vesicle was changed to tetraglyceryl monostearate (TETRAGLYN 1-S), decaglyceryl tristearate (DECAGLYN 3-S), lecithin (SLP white) or sucrose stearate (S-1670) and further, in Examples 25 to 29, the organic solvent used for the preparation was changed from ethanol to isopropyl alcohol (IPA) or tetrahydrofuran (THF), and the formulation amount of each of the components was changed as indicated in Tables 8 and 9.

<Evaluation of Water Dispersibility 6>

The particulate compositions of Examples 25 to 30 and the particles of Comparative Example 5 were dispersed in water, and the mean particle sizes were measured using a dynamic-electrophoretic light scattering photometer (ELSZ, manufactured by Otsuka Electronics Co., Ltd.). The measurement was performed in the same manner as in the above-mentioned "Evaluation of Water Dispersibility 1". In addition, the water dispersibility of each of the particulate compositions of the Examples and that of the particles of the Comparative Example were evaluated based on the same criteria as that of the above-mentioned "Evaluation of Water Dispersibility 1". The results are indicated in Tables 8 and 9 below.

TABLE 8

| Components | Comparative Example 5 | Example 25 | Example 26 | example 27 |
|---|---|---|---|---|
| Cerium oxide B (stearic acid-treated) | 2 g | 2 g | 2 g | 2 g |
| Tetraglyceryl monostearate (TETRAGLYN 1-S) | — | 0.2 g | 0.2 g | — |
| Decaglyceryl tristearate (DECAGLYN 3-S) | — | — | — | 0.2 g |
| Lecithin (SLP white) | — | — | — | — |
| Sucrose stearate (S-1670) | — | — | — | — |
| Organic solvent | — | IPA | THF | IPA |
| Mean particle size in water dispersion (nm) | — | 685.5 | 512 | 536 |

TABLE 8-continued

| Components | Comparative Example 5 | Example 25 | Example 26 | example 27 |
|---|---|---|---|---|
| Evaluation of water dispersibility | — (Powder floating) | ++ | ++ | ++ |

TABLE 9

| Components | Example 28 | Example 29 | Example 30 |
|---|---|---|---|
| Cerium oxide B (stearic acid-treated) | 2 g | 2 g | 2 g |
| Tetraglyceryl monostearate (TETRAGLYN 1-S) | — | — | — |
| Decaglyceryl tristearate (DECAGLYN 3-S) | 0.2 g | — | — |
| Lecithin (SLP white) | — | 0.2 g | — |
| Sucrose stearate (S-1670) | — | — | 0.2 g |
| Organic solvent | THF | THF | Ethanol |
| Mean particle size in water dispersion (nm) | 346 | 458 | 358.8 |
| Evaluation of water dispersibility | ++ | ++ | ++ |

As indicated in Tables 8 and 9, it was found that even if the type of amphiphilic substances was changed, high water dispersibility was obtained by surface treating the solid particles with the amphiphilic substance capable of forming a vesicle in water.

Example 31 and Example 32

The particulate composition of Example 31, in which the surface of untreated cerium oxide B in an amount of 2 g was treated with 0.1 g of the polyoxyethylene-hydrogenated castor oil derivative (HCO-40) as the amphiphilic substance capable of forming a vesicle, was prepared using the same procedures as those in Example 1. In addition, the particulate composition of Example 32, in which the surface of iron-oxide (methicone-treated) in an amount of 2 g was treated with 0.1 g of the polyoxyethylene-hydrogenated castor oil derivative (HCO-40) as the amphiphilic substance capable of forming a vesicle, was prepared using the same procedures as those in Example 19. In addition, 2 g of untreated cerium oxide B was provided as Comparative Example 11, and 2 g of iron oxide (methicone-treated) was provided as Comparative Example 12.

<Measurement of UV-Visible Spectra>

Figure 1A:
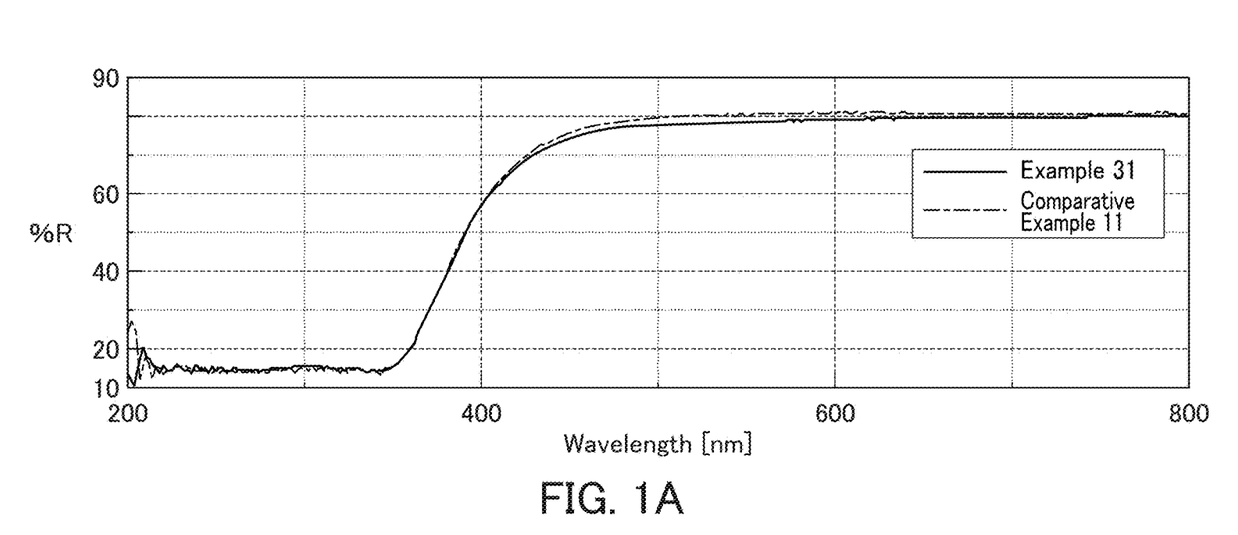
FIG. 1A is UV-visible spectra of the particulate compositions of Example 31 and Comparative Example 11.
Figure 1B:
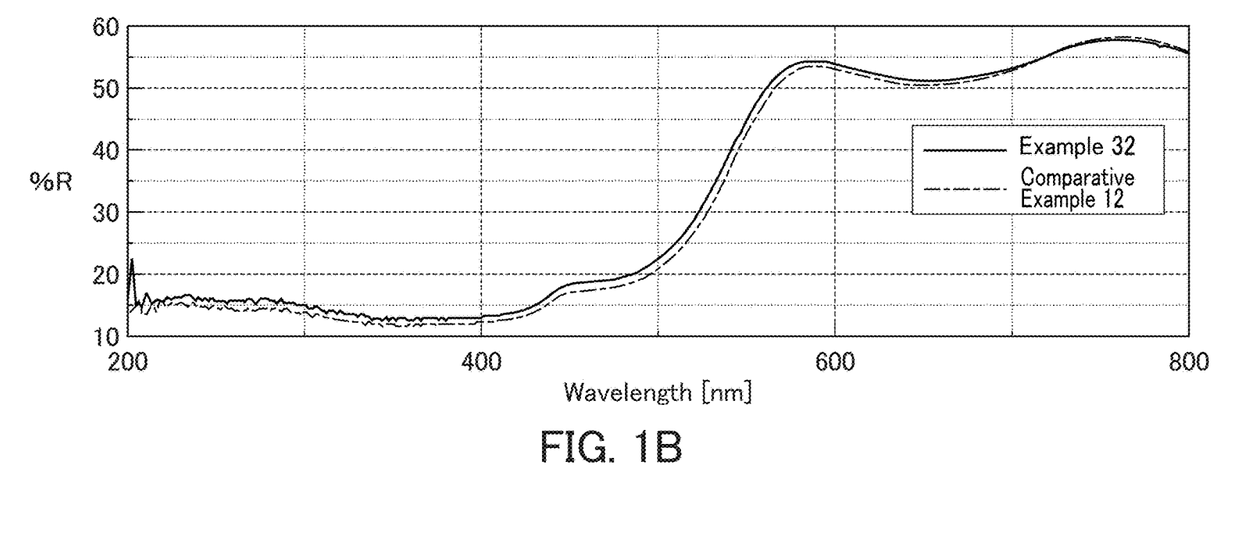
FIG. 1B is UV-visible spectra of the particulate compositions of Example 32 and Comparative Example 12.

The particulate compositions of Examples 31 and 32 and the particles of Comparative Examples 11 and 12 each in a dried state were formed into a pellet-like shape, and ultraviolet-visible spectra were measured using an ultraviolet-visible spectrophotometer (V-570, manufactured by Jasco Corporation). The results are indicated FIG. 1A and FIG. 1B. FIG. 1A is UV-visible spectra for the particulate compositions of Example 31 and Comparative Example 11. FIG. 1B is UV-visible spectra for the particulate compositions of Example 32 and Comparative Example 12.

As indicated in FIG. 1A-FIG. 1B, it was confirmed that the spectra of Example 31 and Comparative Example 11 and those of Example 32 and Comparative Example 12 were substantially the same. Thus, it was found that the physical properties of the solid particles themselves were substantially maintained even when the surfaces of the solid particles were treated with the coating agent used in the present invention.

Example 33 and Example 34

The particulate composition of Example 33, in which the surface of silicon oxide in an amount of 1 g was treated with 1 g of the polyoxyethylene-hydrogenated castor oil derivative (HCO-10) as the amphiphilic substance capable of forming a vesicle, was prepared using the same procedures as those in Example 1. The particulate composition of Example 34 was prepared using the same formulation and procedures as those in Example 33 except that the amount of silicon oxide was halved to the amount of the polyethylene-hydrogenated castor oil derivative (HCO-10) as the amphiphilic substance capable of forming a vesicle.

<TEM Observation>

Figure 2A:
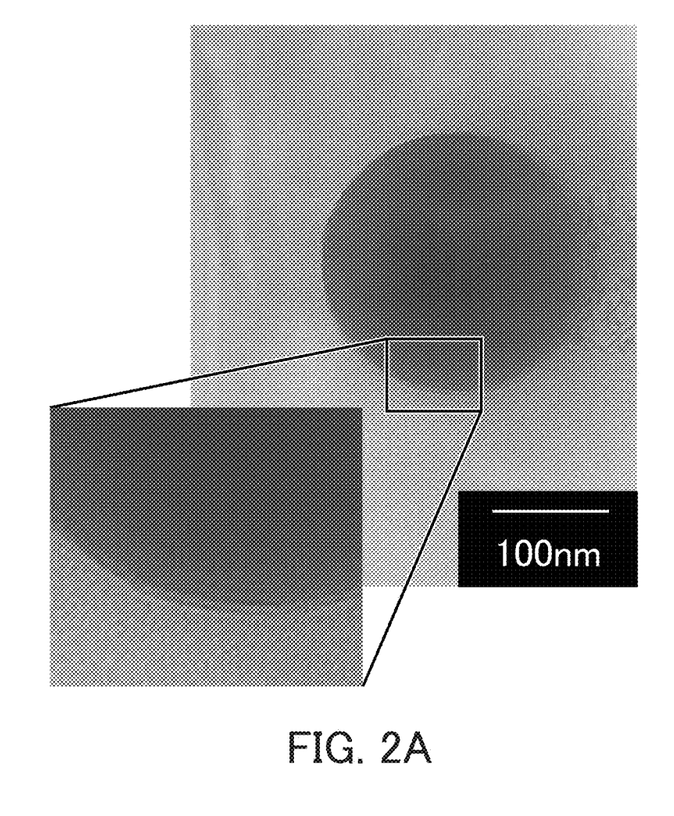
FIG. 2A is a TEM-observation image of the particulate composition of Example 33.

The particulate compositions of Example 33 and Example 34 were observed under TEM (transmission electron microscopy (JEM-2010, manufactured by Nippon Electronics Co., Ltd.)). The results are indicated FIG. 2A-FIG. 2B. FIG. 2A shows an image by TEM observation for the particulate composition of Example 33, and FIG. 2B shows an image by TEM observation for the particulate composition of Example 34.

Figure 2B:
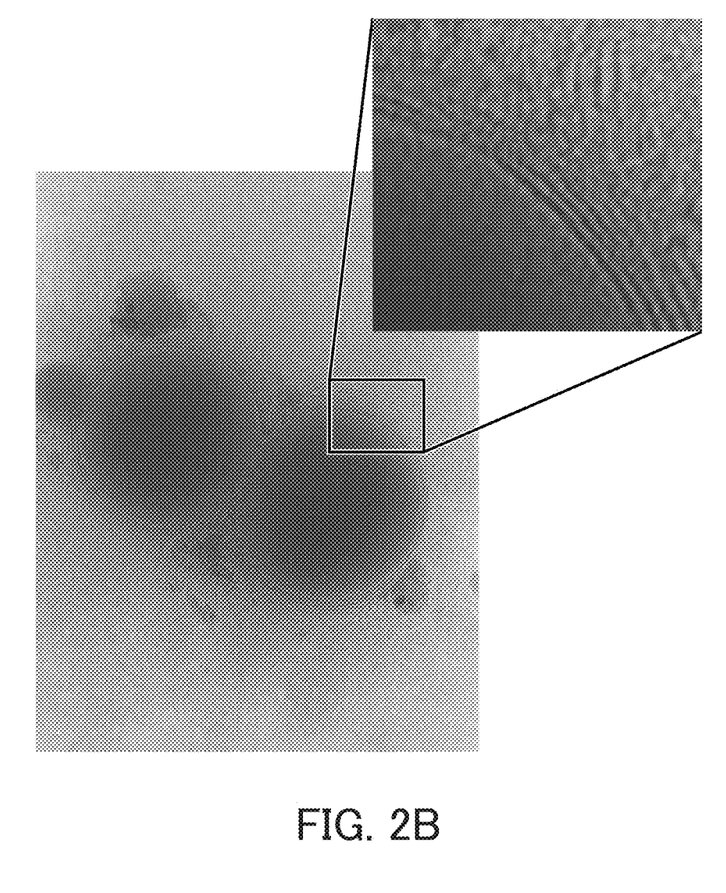
FIG. 2B is a TEM-observation image of the particulate composition of Example 34.

As indicated in FIG. 2A-FIG. 2B, it was confirmed that the coating agent used in the present invention formed a bilayer membrane on the surface of the solid particles to form a multilayer and cover the surface. From this result, it was confirmed that it is desirable in obtaining higher water dispersibility that the coating agent used in the present invention forms three or more bilayers (six or more monolayers) on the surface of the solid particles.

Example 35

The particulate composition of Example 35 was prepared according to the formulation of Table 10 below. Specifically, first, an organic solvent solution of the polyoxyethylene-hydrogenated castor oil derivative (HCO-20) was prepared. This solution containing the polyoxyethylene-hydrogenated castor oil derivative (HCO-20) as the amphiphilic substance capable of forming a vesicle and untreated calcium carbonate having a broad particle size distribution width were added to isopropyl alcohol as the organic solvent, stirred, and agitated by a stirrer for 2 to 3 hours. Thereafter, the mixture was heated while being stirred with a hot stirrer to vaporize the solvent. Then, the mixture was dried in a dryer at 80° C. for 2 to 3 hours to completely remove the solvent and the particulate composition of Example 35 was prepared.

Comparative Example 13

Solid particles were provided in an amount indicated in Table 10 described below and used as the particles of Comparative Example 13.

<Evaluation of Dispersibility in Vaseline>

20 g of Vaseline (melting point 65 to 70° C.) was transferred to a beaker and melted by heating and stirring at 80° C. 20 g of the particulate composition of Example 35 or the particles of Comparative Example 13 was added to this molten Vaseline and stirred for 10 minutes. The obtained sample was observed using an optical microscope while being heated at 80° C. Each sample was evaluated as "++" (good) when the sample had flowability, "+" when the sample had flowability but slight agglomeration was observed, and "−" (poor) when the sample had no flowability. The results are presented in the following Table 10. It should be noted that in this evaluating method, the mass ratio of the particulate composition or the particles is as high as 50 mass %; in such a case, without dispersing ability, the particulate composition or the particles aggregate, resulting in loss of flowability.

<Evaluation of Dispersibility in Solid Paraffins>

50 g of solid paraffin (melting point: 68 to 70° C.) was transferred to a beaker and melted by heating and stirring at 120° C. 50 g of the particulate composition of Example 35 or the particles of Comparative Example 13 was added to this molten paraffin and stirred for 60 minutes. The obtained sample was observed using an optical microscope while being heated at 90° C. Each sample was evaluated according to the same criteria as that in "evaluation of dispersibility in Vaseline" described above. The results are presented in the following Table 10.

<Evaluation of Dispersibility in Liquid Paraffins 1>

50 g of liquid paraffins (melting point: −20 to −25° C.) was transferred to a beaker and 50 g of the particulate composition of Example 35 or the particles of Comparative Example 13 were added and stirred for 60 minutes. The obtained sample was observed using an optical microscope. Each sample was evaluated according to the same criteria as that in "evaluation of dispersibility in Vaseline" described above. The results are presented in the following Table 10.

TABLE 10

| Components | Example 35 | Comparative Example 13 |
|---|---|---|
| Calcium carbonate | 50 g | 50 g |
| HCO-20 | 0.75 g | — |
| Dispersibility in Vaseline | ++ | + |
| Dispersibility in solid paraffins | ++ | — |
| Dispersibility in liquid paraffins | ++ | — |

As shown in Table 10, it was found that high dispersibility in an oily substance was obtained by surface treating the solid particles with the amphiphilic substance capable of forming a vesicle in water.

Example 36

The particulate composition of Example 36 was prepared according to the formulation of Table 11 below. Specifically, first, an organic solvent solution of the polyoxyethylene-hydrogenated castor oil derivative (HCO-40) was prepared. This solution containing the polyoxyethylene-hydrogenated castor oil derivative (HCO-40) as the amphiphilic substance capable of forming a vesicle in water and cerium oxide A with its surface treated with stearic acid were added to ethanol as the organic solvent, stirred, and agitated by a stirrer for 2 to 3 hours. Thereafter, the mixture was heated while being stirred with a hot stirrer to vaporize the solvent. Then, the mixture was dried in a dryer at 80° C. for 2 to 3 hours to completely remove the solvent and the particulate composition of Example 36 was prepared.

Comparative Example 14

Solid particles were provided in an amount indicated in Table 11 and used as the particles of Comparative Example 14.

<Evaluation of Dispersibility in Liquid Paraffins 2>

Dispersibility of the particulate composition of each of the Examples and the particles of the Comparative Example in liquid paraffins was evaluated according to the same criteria as that in "evaluation of dispersibility in Vaseline" described above. The results are presented in the following Table 11.

<Evaluation of Dispersibility in Isopropyl Myristate 2>

50 g of isopropyl myristate was transferred to a beaker and 50 g of the particulate composition of Example 36 or the particles of Comparative Example 14 were added and stirred for 60 minutes. The obtained sample was observed using an optical microscope. Each sample was evaluated according to the same criteria as that in "evaluation of dispersibility in Vaseline" described above. The results are presented in the following Table 11.

<Evaluation of Dispersibility in Tri(Caprylic/Capric) Glyceride>

50 g of tri(caprylic/capric) glyceride was transferred to a beaker and 50 g of the particulate composition of Example 36 or the particles of Comparative Example 14 were added and stirred for 60 minutes. The obtained sample was observed using an optical microscope. Each sample was evaluated according to the same criteria as that in "evaluation of dispersibility in Vaseline" described above. The results are presented in the following Table 11.

TABLE 11

| Components | Example 36 | Comparative Example 14 |
|---|---|---|
| Cerium oxide | 50 g | 50 g |
| HCO-40 | 0.75 g | — |
| Dispersibility in liquid paraffins | ++ | + |
| Dispersibility in isopropyl myristate | ++ | none |
| Dispersibility in tri(caprylic acid/ capric acid) glyceryl | ++ | none |

As indicated in Table 11, it was found that high dispersibility in an oily substance was obtained by surface treating the solid particles with the amphiphilic substance capable of forming a vesicle in water, regardless of whether or not the oily substance has polarity.

The invention claimed is:

1. A particulate composition, comprising solid particles and an amphiphilic substance having three-phase emulsifying ability,
wherein the amphiphilic substance forms bilayers and excludes HCO-10 which is a polyoxyethylene-hydrogenated castor oil derivative,
the surface of the solid particles is coated with three or more bilayers formed of the amphiphilic substance, and a content of the amphiphilic substance ($m_c$ [g]) relative to a mass of the solid particles ($m_s$ [g]) satisfies the following equation, $$m_C \geq 4.77 \times \frac{d_C^{\frac{2}{3}} \times M^{\frac{1}{3}} \times m_S}{d_S \times D},$$

wherein $d_c$ represents a specific gravity of the amphiphilic substance [g/cm$^3$], M represents a molecular weight of the amphiphilic substance [g/mol], $d_s$ represents a specific gravity of the solid particles [g/cm$^3$], and D represents a mean particle size of the solid particles [nm] when dispersed in 99.5% ethanol.

2. The particulate composition according to claim 1, wherein a mean particle size obtained when the particulate composition is dispersed in water or an oily substance is 1.0 times or more and 1.5 times or less of a mean particle size obtained when the solid particles, before being subjected to coating treatment, are dispersed in ethanol.

3. The particulate composition according to claim 1, wherein the solid particles are particles of a metal oxide.

4. A liquid composition comprising the particulate composition according to claim 1 and water or an oily substance comprising the particulate composition.

5. The liquid composition according to claim 4, wherein the surface of the solid particles dispersed in the water or the oily substance is coated with three or more bilayers formed of the amphiphilic substance.

6. The liquid composition according to claim 4, wherein the liquid composition is for cosmetics or paints.

7. A method of producing the particulate composition according to claim 1,
comprising the steps of: preparing a mixture of the solid particles and a solvent in which the amphiphilic substance is dissolved so that the content of the amphiphilic substance ($m_c$ [g]) relative to a mass of the solid particles ($m_s$ [g]) satisfies the following equation, and removing the solvent in the mixture, $$m_C \geq 4.77 \times \frac{d_C^{\frac{2}{3}} \times M^{\frac{1}{3}} \times m_S}{d_S \times D},$$

wherein $d_c$ represents a specific gravity of the amphiphilic substance [g/cm$^3$], M represents a molecular weight of the amphiphilic substance [g/mol], $d_s$ represents a specific gravity of the solid particles [g/cm$^3$], and D represents a mean particle size of the solid particles [nm] when dispersed in 99.5% ethanol.

8. The method according to claim 7, wherein removing the solvent in the mixture is performed by vaporizing the solvent.

9. A method of improving dispersibility of solid particles in water or an oily substance by coating the surface of the solid particles with three or more bilayers formed of amphiphilic substance having three-phase emulsifying ability in the water or the oily substance, the amphiphilic substance excludes HCO-10 which is a polyoxyethylene-hydrogenated castor oil derivative, and a content of the amphiphilic substance ($m_c$ [g]) relative to a mass of the solid particles ($m_s$ [g]) satisfies the following equation, $$m_C \geq 4.77 \times \frac{d_C^{\frac{2}{3}} \times M^{\frac{1}{3}} \times m_S}{d_S \times D},$$

wherein $d_c$ represents a specific gravity of the amphiphilic substance [g/cm³], M represents a molecular weight of the amphiphilic substance [g/mol], $d_s$ represents a specific gravity of the solid particles [g/cm³], and D represents a mean particle size of the solid particles [nm] when dispersed in 99.5% ethanol.

* * * * *